US007931916B2

(12) United States Patent
Gamon et al.

(10) Patent No.: US 7,931,916 B2
(45) Date of Patent: Apr. 26, 2011

(54) COMPOSITION OF BIOCOMPATIBLE MICROPARTICLES OF ALGINIC ACID FOR THE CONTROLLED RELEASE OF ACTIVE INGREDIENTS BY INTRAVENOUS ADMINISTRATION

(75) Inventors: Salvador Grancha Gamon, Granollers (ES); Anna Nardi Ricart, St. Joan Despí (ES); Josep Mariá Suñe Negre, Barcelona (ES); Josep Ramón Tico Grau, Barcelona (ES); Montserrat Miñarro Carmona, Barcelona (ES)

(73) Assignee: Grifols, S.A., Barcelona (ES)

( * ) Notice: Subject to any disclaimer, the term of this patent is extended or adjusted under 35 U.S.C. 154(b) by 0 days.

(21) Appl. No.: 12/634,203

(22) Filed: Dec. 9, 2009

(65) Prior Publication Data

US 2010/0159017 A1    Jun. 24, 2010

(30) Foreign Application Priority Data

Dec. 23, 2008   (ES) .................................. 200803671

(51) Int. Cl.
*A61K 9/14*   (2006.01)
(52) U.S. Cl. ...................................................... 424/486
(58) Field of Classification Search .................. 424/486
See application file for complete search history.

(56) References Cited

U.S. PATENT DOCUMENTS

| 5,417,982 A | 5/1995 | Modi |
| 2004/0005302 A1 | 1/2004 | Hortelano |
| 2007/0224280 A1 | 9/2007 | Lillard et al. |

FOREIGN PATENT DOCUMENTS

| EP | 0635040 B1 | 1/1995 |
| EP | 0 970 705 A1 | 1/2000 |
| EP | 1223917 | 7/2002 |
| ES | 2159523 | 10/2001 |
| ES | 2286040 | 12/2007 |
| WO | WO 91/09119 A1 | 6/1991 |
| WO | WO 96/40829 A1 | 12/1996 |
| WO | WO 2006/028996 A2 | 3/2006 |
| WO | WO 2007/046719 A2 | 4/2007 |
| WO | WO 2007/048599 A2 | 5/2007 |
| WO | WO 2007/129926 A2 | 11/2007 |
| WO | WO 2008/022146 A2 | 2/2008 |
| WO | WO 2008/143812 A2 | 11/2008 |

OTHER PUBLICATIONS

Spanish Search Report dated Apr. 17, 2009 (with English translation of category of cited documents).
Kasper, CK, Hereditary Plasma Clotting Factor Disorders and Their Management 5th ed. WFH, Sam Schulman Ed., 2008. pp. 1-16 and Table of contents.
Bailon, Pascal et al, Bioconjugate Chem. 2001, 12, 195-202.
Perlman, Signe et al, The Journal of Clinical Endocrinology & Metabolism 88 (7): 3227-3235, 2003.
Dennis, Marks S. et al, The Journal of Biological Chemistry vol. 277, No. 38, Issue of Sep. 20, pp. 35035-35043, 2002.
Powell, J.S et al, Journal of Thrombosis and Haemostasis, 6: 277-283, 2007.
Tamilvanan, S. et al, PDA Journal of Pharmaceutical Science and Technology, vol. 62, No. 2, Mar.-Apr. 2008 pp. 125-154.
Sivadas, Neeraj et al, International Journal of Pharmaceutics 358 (2008) pp. 159-167.
Tønnesen, Hanne Hjorth et al, Drug Development and Industrial Pharmacy, 28(6), 621-630 (2002).
Benchabane, Samir et al, Journal of Microencapsulation, Sep. 2007; 24(6): pp. 565-576.
Coppi, Gilberto et al, 2001, Drug Development and Industrial Pharmacy, 27(5), pp. 393-400.
Mladenovska, K., International Journal of Pharmaceutics 342 (2007) pp. 124-136.
Dai, Chuanyun, et al, Colloids and Surfaces B: Biointerfaces 47 (2006) pp. 205-210.
Peirone, Michael et al, J. Biomed. Mater. Res. 42, pp. 587-596, 1998.
García-Martín, Marinee Carmen et al, The Journal of Gene Medicine, J Gene Med 2002; 4: pp. 215-223.
Wong, Joseph et al, Advanced Drug Delivery Reviews 60 (2008) pp. 939-954.
Passirani, Catherine et al, Pharmaceutical Research, vol. 15, No. 7, 1998 pp. 1046-1050.
Ishida, Tatsuhiro et al, Journal of Controlled Release 126 (2008) pp. 162-165.
Koide, Hiroyuki et al, International Journal of Pharmaceutics 362 (2008) pp. 197-200.
Champion, JA, Pharm Res. Aug. 2008; 25(8): 1815-21. Epub Mar. 29, 2008.
Szycher, Michael, High Performance Biomaterials: A Comprehensive Guide to Medical and Pharmaceutical Applications, published by CRC Press, 1991 ISB 0877627754, 9780877627753, 812 pages (filing p. 634 only).
Owens III, Donald E et al, International Journal of Pharmaceutics, vol. 307, Issue 1, Jan. 3, 2006, pp. 93-102.
Parti, R et al (Haemophilia 2000; 6: 513-522.
Erdinc, B.I. [Erdinc B.I. (2007) Micro/nanoencapsulation of proteins within alginate/chitosan matrix by spray drying, Degree Thesis, Queen's University, Kingston, Canada.

(Continued)

*Primary Examiner* — Maryam Monshipouri
(74) *Attorney, Agent, or Firm* — Buchanan Ingersoll & Rooney P.C.

(57) ABSTRACT

Composition of biocompatible microparticles of alginic acid for the controlled release of active ingredients by intravenous administration. The invention relates to a biocompatible composition which comprises microparticles of alginic acid or its salts and an active ingredient. More particularly, the invention relates to microparticles for the encapsulation of an active ingredient to be administered intravenously to a patient who needs it. These microparticles are of a combination of size sufficient to increase the half-life or survival of the active ingredient in blood, with a low uptake in the liver and a fast cell clearance when administered intravenously.

12 Claims, 3 Drawing Sheets

OTHER PUBLICATIONS

European Search Report issued Apr. 1, 2010 in corresponding EP Appln No. 09380191.8.

Isabelle Aynie et al., "Spongelike Alginate Nanoparticles as a New Potential System for the Delivery of Antisense Oligonucleotides", *Antisense & Nucleic Acid Drug Development* vol. 9, No. 3, pp. 301-312 (1999), Mary Ann Liebert, Inc., New York, US.

COMPOSITION OF BIOCOMPATIBLE MICROPARTICLES OF ALGINIC ACID FOR THE CONTROLLED RELEASE OF ACTIVE INGREDIENTS BY INTRAVENOUS ADMINISTRATION

The present invention relates to a biocompatible composition which comprises microparticles of alginic acid or its salts and an active ingredient. More particularly, the present invention relates to microparticles for the encapsulation of an active ingredient to be administered intravenously to a patient who needs it. These microparticles show a combination of size adequate to increase the half-life or survival of the active ingredient in blood, with a low uptake in the liver and a fast cell clearance when administered intravenously. The active ingredient in the composition of the present invention can be a peptide, protein or hormone, of human or animal origin, of natural, recombinant or transgenic nature. Included in examples of active ingredients in the composition of the present invention are blood clotting factors, such as factor VIII, factor IX or factor VIIa.

BACKGROUND OF THE INVENTION

The increase in the half-life in the blood of a therapeutic active ingredient has advantages, including fewer administrations being necessary to gain the desired therapeutic effect. This reduction in the number of administrations is of special importance in drugs for parenteral administration, most especially in those for intravenous use and of special relevance to long-term medications such as, for example, those for the treatment of chronic disorders.

The current tendency is, as far as possible, to administer active ingredients by routes which do not need intravenous access, because of complexity and inconvenience for the patient when this method is used. However, there is a series of active ingredients for which there is at present no alternative to intravenous administration. Included in these are active ingredients of great size and complexity, such as biological or biotechnological products, which include proteins and hormones.

One example of a chronic therapeutic condition where the repeated intravenous administration of complex active ingredients is necessary is haemophilia. Haemophilia is a hereditary disease featuring the appearance of internal and external bleeding due to the total or partial deficiency of proteins related to the clotting of blood. Haemophilia A features a deficiency of clotting Factor VIII, which impedes the normal generation of thrombin, making it difficult for the blood to clot normally as a result. In the case of haemophilia B, the deficiency of Factor IX causes a similar clinical state.

For the treatment of haemophilia, the first therapeutic option consists of replacing the absent protein (FVIII or FIX) by the administration of a therapeutic concentrate containing this factor. Another therapeutic option to obtain correct haemostasis in haemophilia is the administration of FVIIa, which has the ability to generate thrombin in the absence of FVIII or FIX. However, this type of treatment is usually limited to cases where treatment with FVIII or FIX is problematic or has proved ineffective, such as for example in patients who have had an inhibitory immunological response to these active ingredients. To date, none of these products has been successfully administered by any method of administration except intravenous, given its structural complexity and low epithelial permeability.

Therefore, patients affected by haemophilia require intravenous administrations repeated with a frequency determined by its half-life in the plasma. In the case of FVIII the half-life is about twelve hours. This implies, according to the monograph of the World Federation of Haemophilia (Casper, C K, Hereditary Plasma Clotting Factor Disorders and Their Management 5th ed. WFH, Sam Schulman Ed., 2008), that for a primary prophylaxis regime, i.e., for the prevention of bleeding in children without articular damage a dose of about 20 U/kg every 48 hours is used, sufficient to maintain a level of plasma FVIII of more than 1% of the normal value. Essentially, this treatment changes a person with severe haemophilia into one with slight or moderate haemophilia. In the case of FIX, the half life is about 26 hours, so that for primary prophylaxis doses of about 40 U/kg twice a week can be administered in order to maintain a minimum level of 1%.

It has to be taken into account that prophylaxis from an early age (about age one year or at the start of crawling) is the standard of care required in order to avoid articular damage in cases of severe haemophilia.

Consequently, haemophilia is a clear example where an increase in the half-life of the active ingredient would provide a substantial improvement in the patient's quality of life, as it would reduce the number of intravenous administrations, especially difficult in children of a young age.

Other examples of long-term treatments with intravenous administration products are for example, the use of immunoglobulins (IgG) in primary immunodeficiencies and the use of antithrombin III (AT) and alpha-1 antitrypsin (AAT) in congenital deficiencies.

There are numerous technological approaches aiming at extending the plasma half-life of these types of active ingredients. One of the most studied has been the derivatisation of proteins with compatible polymers, as is the case of polyethylene glycol (PEG). This technology consists of the practice of carrying out a chemical reaction to join PEG chains covalently to protein amino acids. This technique has proved useful in the case of hormones and peptide chains of small size, such as interferon, since for compounds of this type the principal mechanism of elimination is renal clearance, easily controllable by a simple increase in size (Bailon Pascal et al, Bioconjugate Chem. 2001, 12, 195-202). However, it is still to be decided whether it can be used in more complex active ingredients, as they are based on the external modification of the protein structure to be treated. In addition, covalent bonds of this type with the protein considerably reduce the biological activity of the treated hormone or protein.

Another alternative to modify the half-life has been the addition or modification of the sugar residues naturally present in proteins or hormones (Perlman Signe et al, The Journal of Clinical Endocrinology & Metabolism 88 (7): 3227-3235, 2003). This procedure claims to alter the protein, by modifying its recognition by the receptors involved in its degradation. However, the inherent risks of this alteration are obvious, given the high immunogenic potential of the glycosylations present in the proteins.

A third line of action has been to obtain chimeric proteins where the active sequence of a protein of interest is expressed, bonded to sequences of plasma proteins which have a considerable half-life, as is the case of albumin or fragments of immunoglobulins (Dennis, Marks S. et al, The Journal of Biological Chemistry vol. 277, No. 38, Issue of September 20, pp. 35035-35043, 2002). However, this technology has as its principal disadvantage, in addition to the expected immunogenicity associated with exposing patients to proteins not present in nature, loss of efficacy of the protein upon the modification of its structure in such a dramatic way.

Another possibility investigated to extend the half-life of complex active ingredients has been the co-administration of the product with a liposome stabilised with PEG. This technique is based on the affinity of the active ingredient for PEG, which allows a reversible association between the protein and the liposome. This transitory association must provide an increase in the half-life of the active protein ingredient, since liposomes stabilised with PEG stay in circulation for a long time. However, it has not been possible to corroborate this hypothesis in practice, as this system has proved to be ineffective in extending the half-life of FVIII in haemophilia patients (Powell J. S et al, Journal of Thrombosis and Haemostasis, 6: 277-283, 2007).

To date, no system amongst those previously described has been able to significantly modify the half-life, with the exceptions described where the introduction of structural modifications and alterations make their application unviable or very complex for the treatment of human pathologies.

The controlled release of therapeutic agents encapsulated in biodegradable polymeric microspheres has been extensively studied. The microencapsulation of the active ingredient in biodegradable polymers allows the release of the drug to be controlled. This approach has recently been applied in controlled release formulations for subcutaneous use based on derivatives of lactic and glycolic acids. These formulations have been used successfully in the encapsulation of a wide variety of active ingredients, including cytostatics, anti-inflammatories, peptides and hormones, inter alia (Tamilvanan S. et al, PDA Journal of Pharmaceutical Science and Technology, vol. 62, No. 2, March-April 2008 pp. 125-154).

Pankaj (U.S. Pat. No. 5,417,982) describes the use of lactic and glycolic acid microspheres for the controlled release of hormones by oral administration. Although Pankaj describes the possibility of obtaining an injectable product, it is very unlikely that this invention can be administered intravenously, given the requirements of this method of administration, and in any case, this invention does not anticipate the use of alginates for this purpose.

Sivadas (Sivadas Neeraj et al, International Journal of Pharmaceutics 358 (2008) pp. 159-167) describes the use of different polymers, including hydroxypropyl cellulose, chitosan, hyaluronic acid, gelatine, ovalbumin and glycolic polylactic acid, as vehicles for the encapsulation of proteins for their administration by inhalation.

One disadvantage of the use of lactic and glycolic acid derivatives is the need to make the preparations in the presence of organic solvents, some of them of known toxicity, such as polyvinyl alcohol, which exhibit incompatibilities with the conservation of the biological activity of complex active ingredients such as proteins and hormones.

The use of these polymers also results in highly hydrophobic particles, which, as is discussed below, are rapidly eliminated from the circulation by cellular uptake mechanisms. An additional disadvantage is the creation of a locally very acid environment around the particle at the time of its dissolution and, therefore, at the time when the active ingredient is released. This is due to the fact that the polymer decomposes in lactic acid and glycolic acid, which creates an extremely acidic environment around the particle in dissolution. It is this acid environment which can damage sensitive active ingredients and particularly those which have complex amino acid structures with labile biological activity.

Alginates have many applications in the food and pharmaceutical industries and in the chemical industry in general. This wide variety of applications is defined by their hydrocolloid property, i.e., their ability to hydrate themselves in water so as to form viscous solutions, dispersions or gels. This feature gives alginates unique properties as thickening agents, stabilising agents, gelling agents and film formers.

One area where the properties of alginates have been widely exploited has been in the encapsulation of active ingredients in particular in order to improve their solubility, or to assist the administration of drugs (Tønnesen, Hanne Hjorth et al, Drug Development and Industrial Pharmacy, 28(6), 621-630 (2002)) by various routes. Amongst these is the use of oral administration given the mucoadhesive properties of alginate. The subcutaneous method has also been examined. However there is no history of intravenous use due to the strict requirements of this route of administration.

For example, Benchabane (Benchabane, Samir et al, Journal of Microencapsulation, September 2007; 24(6): pp. 565-576) describes the use of alginates in the production of albumin microcapsules by "spray-drying" for oral administration. In a similar antecedent, Coppi (Coppi, Gilberto et al, 2001, Drug Development and Industrial Pharmacy, 27(5), pp. 393-400) demonstrates the formation of microspheres crosslinked with calcium and chitosan for the oral administration of proteins. In both cases, alginate acts as a protector of protein against the proteolytic degradation which occurs naturally during gastric digestion.

Further, Mladenovska (Mladenovska, K., International Journal of Pharmaceutics 342 (2007) pp. 124-136) describes obtaining microparticles of alginate/chitosan for colonic administration.

Sivadas (Sivadas Neeraj et al, International Journal of Pharmaceutics 358 (2008) pp. 159-167) also mentions the use of alginates as a vehicle for the encapsulation of proteins for administration by inhalation.

Apart from the direct administration of active ingredients, alginates have also been suggested as vehicles for the administration of complex therapeutic forms. For example, in patent WO 2006/028996 A2 the use of alginate and Emulsan for the transport of detoxifying agents of bacterial toxins is described.

Another example is the use of alginate in the encapsulation of multivesicular liposomes (Dai, Chuanyun, et al, Colloids and Surfaces B: Biointerfaces 47 (2006) pp. 205-210) or live cells (European Patent, publication number: 2 159 523). In this case, the administration of live cells has as its objective their application in regenerative medicine or gene therapy (WO 2007/046719 A2; Peirone, Michael et al, J. Biomed. Mater. Res. 42, pp. 587-596, 1998; García-Martín, Carmen et al, The Journal of Gene Medicine, J Gene Med 2002; 4: pp. 215-223). Curiously, García-Martín (García-Martín, Carmen et al, The Journal of Gene Medicine, J Gene Med 2002; 4: pp. 215-223) describes the possible application of the administration of genetically modified live cells for the treatment of haemophilia A, exemplifying the medical relevance of the problem. In this case, alginate microcapsules which contain live cells are implanted intraperitoneally by the introduction of a catheter. In this case, both the objective of the treatment and the method of administration—non-intravenous—are radically far from the present invention.

In spite of this wide experience in the use of polymers for the encapsulation of complex active ingredients, such as proteins, there are no references which can resolve the problems associated with the intravenous administration of these products. As Wong et al describe (Wong, Joseph et al, Advanced Drug Delivery Reviews 60 (2008) pp. 939-954) there are only three approved products which use particle suspensions for their intravenous administration. None of them include the use of alginates in their composition. In all cases, an increase in half-life is not sought, but an improvement in the solubility of the product.

The difficulty of effectively administering microparticles intravenously can be expressed in (a) the basic aspects of design of the product, such as the size of the particle and distribution, absence of organic solvents, and also the homogeneity, viscosity and "syringeability" of the suspension—understanding as "syringeability" the ease of suction and injection of the product; (b) the technical aspects of production and preparation on an industrial scale, such as the uniformity of the dose, the unwanted crystallisation of salts in the case of products obtained by solvent precipitation, the sterility and apyrogenicity of the product; and (c) biological aspects, such as the non-deliberate alteration of the pharmacokinetic and pharmacodynamic profile, alteration of the biodistribution, the bioaccumulation of the polymer, phagocytic activation, toxicity and effects of embolisation or activation of the complement.

In this connection, one of the most significant problems in the development of these products is its fast clearance by the mononuclear phagocyte system (MPS), previously called reticuloendothelial system (RES), which includes all the cells derived from the monocytic precursors of the bone marrow, the monocytes of the peripheral blood and the macrophages or histiocytes of the various organs and tissues. Amongst the latter must be mentioned, because of their importance in the clearance of microparticles in plasma, the Küpfer cells of the liver and the macrophages distributed in the spleen and the bone marrow (Passirane, Catherine et al, Pharmaceutical Research, Vol. 15, No. 7, 1998 pp. 1046-1050).

It has been widely described that after the intravenous administration of nano- or micro-particles they are rapidly opsonised by the proteins of the plasma. These proteins absorbed in their surface induce recognition and uptake by the MPS cells (Passirane, Catherine et al, Pharmaceutical Research, Vol. 15, No. 7, 1998 pp. 1046-1050).

A similar effect has been observed in liposomes (Ishida, Tatsuhiro et al, Journal of Controlled Release 126 (2008) pp. 162-165), where a phenomenon known as Accelerated Blood Clearance (ABC) has been described. Both in the case of polymeric microparticles and in that of liposomes, the opsonisation phenomena are also directly related to the activation of the complementary system (Ishida, Tatsuhiro et al, Journal of Controlled Release 126 (2008) pp. 162-165; Koide, Hiroyuki et al, International Journal of Pharmaceutics 362 (2008) pp. 197-200).

In practice, this phagocytosis phenomenon prevents the development of drugs with an extended half-life based on microparticles administered intravenously, since the increase in size associated with encapsulation does not just increase but on occasions causes accelerated degradation. Obviously, this phenomenon is only observed by means of in vivo experimentation, which involves studies of pharmacokinetics in animals.

The relationship between this clearance via phagocytosis and the size of the particle has been widely documented. Champion (Champion, J A, Pharm Res. 2008 August; 25(8): 1815-21. Epub 2008 Mar. 29) specifically describes the relationship between the phagocytosis experienced by polymeric microparticles and their size, observing a maximum effect between 2-3 µm. Other features which define the uptake of microparticles by the MPS in vivo are the hydrophobicity of the particles and their Zeta Potential (Z Potential) (Szycher, Michael, High Performance Biomaterials: A Comprehensive Guide to Medical and Pharmaceutical Applications, published by CRC Press, 1991 ISB 0877627754, 9780877627753, 812 pages).

Z Potential is a property of the particles. Specifically, disperse particles tend to become electrically charged by the adsorption of ions from the external phase, or by ionisation of functional groups on their own surface. One consequence of this is that a layer of counterions called the Stern layer will appear back to back with the particle in the environment of a negatively charged dispersed particle. A diffused layer appears on said stern layer featuring the presence of mobile charges (of both signs) which will counteract the charge of the particle, as a function of the distance to the same. Z Potential is what we call the difference in potential between the layer of counterions and the point of electrokinetic neutrality.

Z Potential values are crucial for the stability of the majority of dispersed systems, since the latter will regulate the degree of repulsion between dispersed particles of similar charge, preventing said particles from coming too close to one another and the forces of inter-particle attraction, caused by the coalescence phenomena, from becoming predominant. As regards the Z potential, it has been disclosed (Szycher, Michael, High Performance Biomaterials: A Comprehensive Guide to Medical and Pharmaceutical Applications, published by CRC Press, 1991 ISB 0877627754, 9780877627753, 812 pages) that partially negative Z potentials close to 0 reduce phagocytosis.

Moreover, hydrophobicity also assists the opsonisation and uptake of the particles. This is of particular interest, since particles derived from polylactic and glycolic acids are, for example, highly hydrophobic.

One approach achieved to extend the half-life in plasma of microparticles and liposomes was the introduction, onto the surface thereof, of charged polymers which are able to modify their charge and generate a hydrophilic surface layer to protect them from opsonisation and phagocytosis. Amongst them is the use of polyethylene glycol (PEG) (Ishida, Tatsuhiro et al, Journal of Controlled Release 126 (2008) 162-165; Owens III, Donald E et al, International Journal of Pharmaceutics, volume 307, Issue 1, 3 Jan. 2006, Pages 93-102) or heparin (Passirane, Catherine et al, Pharmaceutical Research, Vol. 15, No. 7, 1998 pp. 1046-1050).

This approach complicates and makes difficult the development of a pharmaceutical product because of the increase in the complexity of the system. In addition, as has been previously discussed, the use of PEG-liposomes has proved to be ineffective in extending the half-life of a complex protein such as FVIII (Powell J. S et al 2007, Journal of Thrombosis and Haemostasis, 6: pp. 277-283).

In the case of microparticles, in order to obtain a viable product for intravenous administration it would be necessary to have hydrophilic particles with a suitable combination of size and Z potential.

Terrence (European Patent, Publication Number: 2 286 040, European Application Number: 00973477.3) describes the use of polymers as a system of administration capable of increasing the half-life of the active encapsulated ingredients. For this purpose, this invention requires the use of (1) a first water-soluble polymer, (2) at least one anionic polysaccharide as first complexing agent and (3) a divalent cation as a second complexing agent. As has been observed, the invention mentioned is technically complex and difficult to use in practice. In contrast, in the present invention the controlled release of the active ingredient is achieved with far simpler microparticles, which involve the use of a single polymer that possesses all the properties necessary for its application. Furthermore, Terrence's invention does not demonstrate the compatibility of its preparation for intravenous use by size, or explain or illustrate how to avoid cellular phagocytosis.

Alginate, unlike other polymers with PLA or PLGA, is hydrophilic. Particles generated in the present invention have been shown to have partially negative Z potentials sufficient to prevent the aggregation of particles, but neutral enough to provide a low opsonisation profile.

The maximum sizes of particle acceptable for intravenous administration are around 5 µm. This is demonstrated by the existence of registered drugs which use albumin marked for diagnosis by ultrasounds (Optison, data sheet 28) with an average size of 3.0-4.5 µm.

Alginate is biocompatible, and has been used extensively for oral administration in humans, given its wide use in the food industry. When injected intravenously as a non-particulate polymer, it is eliminated in a biphasic form with half-lives of 4 and 22 hours (Hagen, A. et al, European Journal of Pharmaceutical Sciences, Volume 4, Supplement 1, September 1996, pp. 100-100 (1)) without adverse effects being observed. Alginate is eliminated via urine.

In addition, the fact that it is a water-soluble polymer assists its compatibility with complex proteins, as these latter are its natural solvent.

The present invention relates to a composition comprising microparticles of alginic acid or its pharmaceutically acceptable salts by which a controlled release is achieved, and achieves an increase in the half-life of the active ingredients administered intravenously, and results in a lower frequency of application and achieves more stable levels of active ingredient in the blood, thus potentially reducing the peaks and troughs typical in the concentration of the active ingredient, which occur as a result of the periodical infusion of the same.

The present invention describes hydrophilic microparticles of alginate with a combination of size suitable for intravenous infusion and physio-chemical characteristics suitable for preventing the rapid phagocytosis of the same, allowing a controlled release of complex active ingredients.

DESCRIPTION OF THE INVENTION

Alginic acid and its salts (ammonium alginate, calcium alginate, potassium alginate, sodium alginate and propylene glycol alginate) are among the polymers most used and studied in the encapsulation of active ingredients due to their physicochemical and biochemical properties. They are polysaccharides of natural origin, commercially produced from algae or bacteria.

Alginates are alginic acid salts, a linear polysaccharide made up of two monomer units, β-(1-4)-D-mannuronic (M) acid and α-(1-4)-L-guluronic (G) acid. These are grouped in blocks forming a wide variety of sequences, the most common being G, M and MG.

In the presence of multivalent cations like calcium ($Ca^{++}$), strong bonds are made between contiguous G blocks forming an extended network of alginates. Calcium ions are situated as bridges between the groups with a negative charge of guluronic acid. In some formulations they are often accompanied by other polysaccharides such as chitosan. Chitosan is a linear polysaccharide composed of randomly distributed chains of β-(1-4) D-glucosamine (deacetylated units) and N-acetyl-D-glucosamine (acetylated unit).

In some alginate formulations albumin can be used as the substance of charge, preferably sterile and pyrogen-free human albumin, which can also act as a protector of the active ingredient in the process of manufacture or as a stabiliser during the long-term conservation of the product.

The active ingredient which release in plasma is intended to be modified can be a complex and labile active ingredient. More specifically, the active ingredient features exhibits biological activity. This biological activity can be developed through enzymatic activity, transport, molecular interaction or binding with a ligand. In both cases, it would be a question of active ingredients labile or sensitive to energetic conditions of manufacture in temperature, pressure and/or nonpolar environments amongst others, since small structural changes can lead to an irreversible loss of biological activity.

As examples of active ingredients with biological activity, human peptide hormones such as melatonin, serotonin, thyroxin, epinephrine, norepinephrine, dopamine, adrenocorticotropic hormone, angiotensinogen and angiotensin, vasopressin, atriopeptin, calcitonin, erythropoietin, follicle stimulating hormone, glucagon, human chorionic gonadotropin, human placental lactogen, growth hormone, inhibin, insulin, insulin-type growth factor (or somatomedin), luteinising hormone, melanocyte-stimulating hormone, oxytocin, prolactin, thrombopoietin, neuropeptide Y, histamine, together with their derivatives can be mentioned.

Other examples can be biologically active proteins such as albumin, alpha 1-antitrypsin, alpha-acid glycoprotein, alpha-2-macroglobulin, antithrombin, haptoglobin, ceruloplasmin, lipoproteins, transferrin, plasminogen, fibrinogen, complementary proteins, clotting factors, and immunoglobulins, amongst others.

The fact that these active ingredients are biologically active makes them especially vulnerable to a possible loss of functionality as a result of minor structural damage. This structural damage can be associated with temperature, pressure, polarity of the medium, osmolality, presence of oxygen, agitation, etc.

In this connection, clotting factor VIII stands out amongst these active ingredients because of its extreme lability. Due to its structural complexity, it is very difficult to adequately stabilise the biological activity of FVIII, especially in its purified form. For example, Parti R et al (Haemophilia 2000; 6: 513-522) explain how even in its lyophilised form, the biological activity of FVIII begins to be compromised at temperatures of above 40° C. This instability is most evident when FVIII is in solution, where even at 25° C. signs of instability are observed. In the case of Factor IX and of Factor VIIa sensitivity to external factors such as temperature is also known.

In this regard it must be noted that the manufacturing process applied allows therapeutic preparations with biological activity of FVIII to be obtained. This means that the method is applicable to active ingredients exhibiting biological activities which are difficult to stabilise, and, therefore, that the present invention is applicable to ingredients which are as labile as FVIII. By extension, the present invention is applicable to ingredients that are more stable than FVIII. As a result, clotting factors are a clear example of an active ingredient which can benefit from the application of the formulation as described in the present invention.

In the present invention the active ingredient included in the polymer microsphere can thus be a peptide, a protein or a hormone exhibiting biological activity. Preferably, the active ingredient is a clotting factor and more preferably, the active ingredient is the VIII factor, the von Willebrand factor, the complex formed by the VIII factor and the von Willebrand factor, the IX factor or the VIIa factor.

These ingredients can be of human, animal, recombinant or transgenic origin. In the latter cases, the synthesised molecule can be a reproduction of the natural molecule or be deliberately modified.

Obtaining the Composition

Microencapsulation is a process of coating molecules, solid particles or liquid globules, with materials of a different nature, in order to create particles of micrometric size. The products resulting from this technological process are named microparticles, microcapsules or microspheres.

There are several microencapsulation techniques:
Microencapsulation by chemical methods:
  Interfacial polymerisation
Microencapsulation by physicochemical methods:
  Evaporation of solvent
  Coacervation
  Gellification
  Chelation
  Formation of vesicles
Microencapsulation by mechanical methods:
  Extrusion
  Co-extrusion
  Spray drying
  Spray chilling The chosen technique for the manufacture of microparticles described in the present invention is spray drying, as described in Erdinc B. I. [Erdinc B. I. (2007) Micro/nanoencapsulation of proteins within alginate/chitosan matrix by spray drying, Degree Thesis, Queen's University, Kingston, Canada]. This manufacturing technique features a single stage and microparticles are obtained as the final product.

The manufacturing process of a biocompatible composition for intravenous administration which includes microparticles of alginic acid or its salts for the controlled release of an active ingredient of the present invention is characterized by the stages of:
  spraying, in which the solution/suspension/emulsion containing the active ingredient and the polymer is pumped through a nozzle and is dispersed in the form of drops,
  drying in the drying chamber, where the hot air assists the evaporation of the solvent from the drops, and
  collection of the encapsulated product
this procedure being performed at a temperature of between 140 and 180° C. with a supply flow rate between 35 and 40 m$^3$/h, an injection flow rate between 3.5 and 5 ml/min and a pressure between 4 and 6 psi.

Under these conditions it is possible to obtain particles with a size of less than or equal to 5 µm, preferably between 1 and 4.5 µm and maintain the activity of the active ingredient. In addition, the average size of the particles can be improved in an optional process of homogenisation of the emulsion before the spray stage. This additional homogenisation process is carried out by means of pressure, for example between 1500 and 2000 psi.

The encapsulation of active ingredients by means of spray drying is a continuous process in which a solution or emulsion is dehydrated, recovering a solid formed by microparticles at the end of the process.

To this end, the fluid containing the active ingredient is driven mechanically at a predetermined injection flow rate towards a nozzle or rotating disk in which it is sprayed in millions of very small drops. The size of the drops is determined in large measure by the pressure of the gas that causes the spray of the fluid. This process takes place in a closed chamber where a stream of controlled gas, which is usually air, circulates continuously at a predetermined speed of intake and at a controlled temperature.

As a result of the spraying, the fluid greatly increases its contact surface area with the air, so that when faced with the current of drying air there is a rapid evaporation of the fluid solvent, usually water. This rapid evaporation causes the internal cooling of each small drop due to the heat needed for the change in state. In this way it is possible to carry out fast drying whilst minimising the thermal shock to the active ingredient. Upon completion of the process, the product is collected in solid form.

Description of the Composition

The microparticles obtained are distinguished by determining their particle average size, their Z potential and biological activity. The size of particle is determined with a Beckman Coulter LS13320 device by a diffraction laser.

As it is a question of intravenous administration, it is necessary for the particle size to be less than or equal to 5 µm, preferably between 1 and 4.5 µm, because higher particle sizes could cause the formation of thrombi.

The Z potential, which is determined with a Malvern Zetasizer device, is one of the fundamental parameters controlling the interaction of the particles in suspension. It is determined by the nature of the particle surface and the dispersion medium. In this case the optimal values are those above −30 mV since this ensures repulsion between particles and absence of aggregates. It has been shown that microparticles with Z potentials close to 0, preferably between −30 mV and 0, have low liver uptake and cell clearance levels. (Szycher, Michael, High Performance Biomaterials: A Comprehensive Guide to Medical and Pharmaceutical Applications, published by CRC Press, 1991 ISB 0877627754, 9780877627753, 812 pages).

Use of the Composition

The pharmaceutical forms of modified or controlled release are those designed in such a way as to change the speed and/or the place of release of the active substance or substances in relation to the pharmaceutical form of conventional release, administered in the same way.

In the present invention it has been observed how the encapsulation of active ingredients exhibiting biological activity, such as proteins, and more specifically, clotting factors, allows a controlled release in an in vitro release model. Factor VIII is notable for its extreme sensitivity to external factors given its structural complexity. In fact, even freezing FVIII in human plasma itself, its natural matrix, causes a partial loss of biological activity (Bravo, M. I. et al, Pharmeuropa Scientific Notes, 2006-1 pp. 1-5).

So when the microparticles containing human FVIII described in the present invention are placed in a continuous flow cell in a similar environment to human plasma, a delay has been observed, compared with the unencapsulated product, in the release of FVIII in the medium.

Similarly, intravenous administration of FVIII-containing microparticles of the present invention in rabbits, results in consistent and significant extension of the half-life of FVIII in plasma, as compared to the conventional product. Furthermore, no adverse effects were observed in animals that might indicate a toxic effect associated with the formulation described.

The in vivo pharmacokinetics data are very significant because they prove without doubt that the effect of opsonisation and accelerated uptake for the MPS has been dealt with properly for the formulation of the invention.

The present invention can be used in the treatment of various pathologies that require the intravenous administration of complex ingredients, which can include for example, bleeding disorders and clotting disturbances, hormonal disorders, etc. In these cases, a significant extension of half-life would be achieved, which for example in the case of FVIII, could include reducing the number of administrations for maintaining a primary prophylaxis regime, for example, weekly administration.

A possible drawback associated with the use of hydrophilic polymers may be the partial dissolution of the microparticle during the period of time between suspension of the product in an aqueous vehicle of administration, for example, water for non-pyrogenic and sterile injection and the time of the intravenous infusion. This type of disadvantage can be overcome for example with the use of partially apolar biocompatible solutions, such as ethanol, propylene glycol, polyethylene glycol, dimethylsulphoxide, N-methyl-2-pyrrolidone, glycofurol, isopropylidene-glycerol, glycerol formal or acetone (Mottu F et al. Journal of Pharmaceutical Science & Technology 2000 Vol. 54, No. 6, 456-469), amongst others, as vehicles of resuspension and administration of the microparticles described in the present invention.

The invention can be produced, for example, in the form of a dehydrated or freeze-dried product packed in a vacuum or inert atmosphere, allowing long-term stability in varying temperature conditions, for example, between 2° C. and 40° C. The product thus preserved can be administered intravenously after reconstitution with a solvent which can be water for injection, or a saline solution, or a mixture or an aqueous saline solution with a variable content, for example between 0.5% and 50% of biocompatible solvents such as for example ethanol, propylene glycol, polyethylene glycol, dimethylsulphoxide, N-methyl-2-pyrrolidone, glycofurol, isopropylidene-glycerol, glycerol formal or acetone, amongst others.

Advantages Over the Prior Art

The present invention describes the production of hydrophilic microparticles of alginate with a combination of a size suitable for intravenous infusion and physicochemical features suitable for preventing their rapid phagocytosis, allowing an extension of the half-life of complex active ingredients.

Alginate is biocompatible and is eliminated via urine, and has no association with any known effect of toxicity. Due to its features, the present invention is compatible with the administration of proteins and complex active ingredients.

This invention can overcome all the disadvantages that have made a controlled administration intravenous system impractical, thus decreasing the number of administrations necessary for treatment with unchanged active ingredients for intravenous use. In this regard it should be noted that the present invention does require any modification of an active ingredient, in the amino acid sequence, glycosylations or introduction of synthetic derivatives.

EXAMPLE 1

Preparation of the Microparticles

Figure 1:
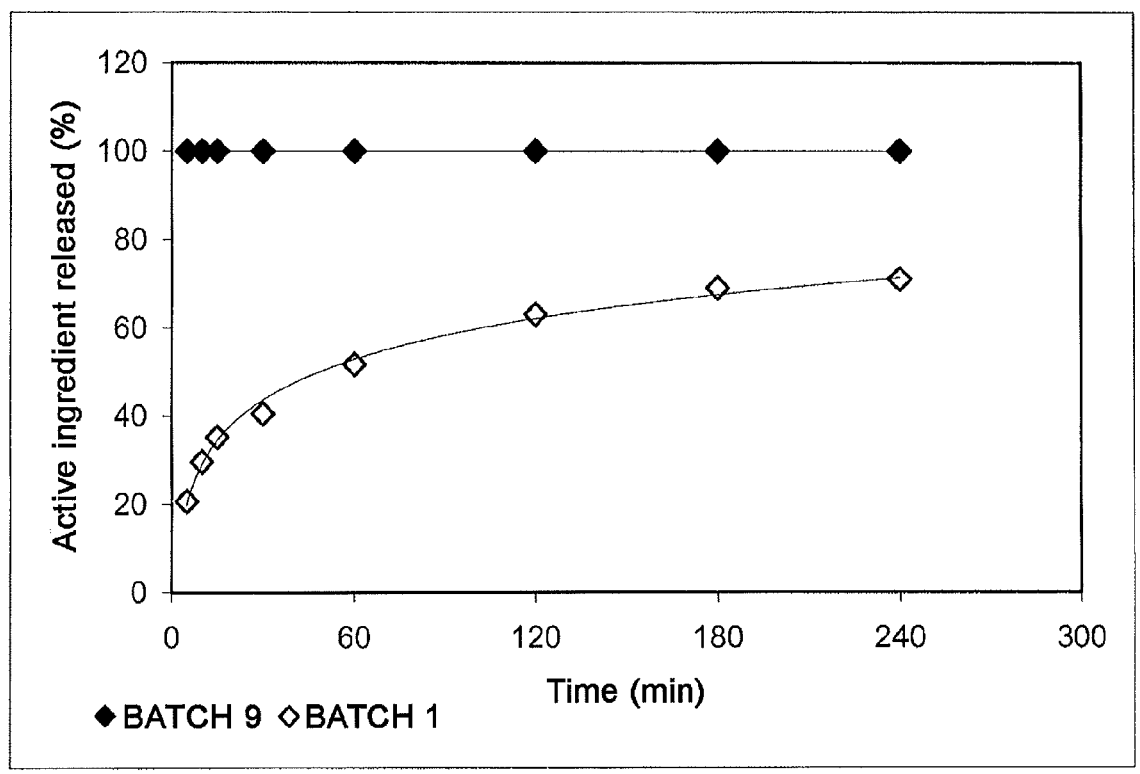
FIG. 1 shows a comparative graph of the results of the in vitro release tests of BATCH 9 and BATCH 1.
Figure 2:
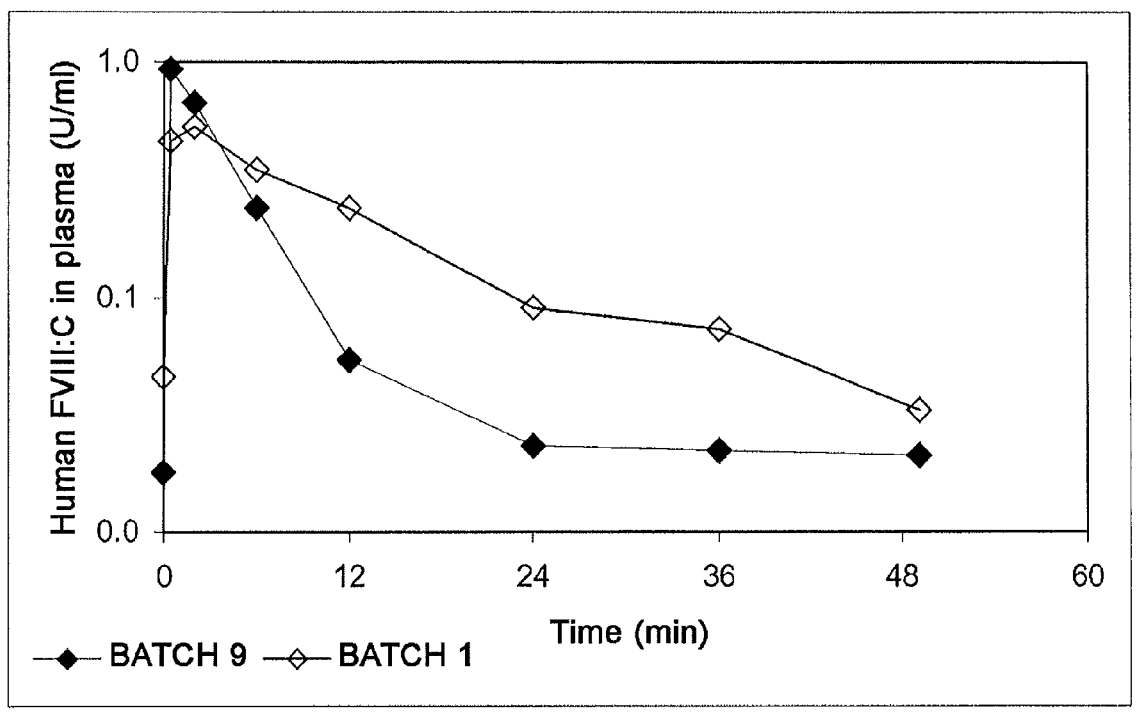
FIG. 2 shows the pharmacokinetics of human FVIII:C in rabbit plasma after the administration of unencapsulated FVIII and after the application of the composition.
Figure 3:
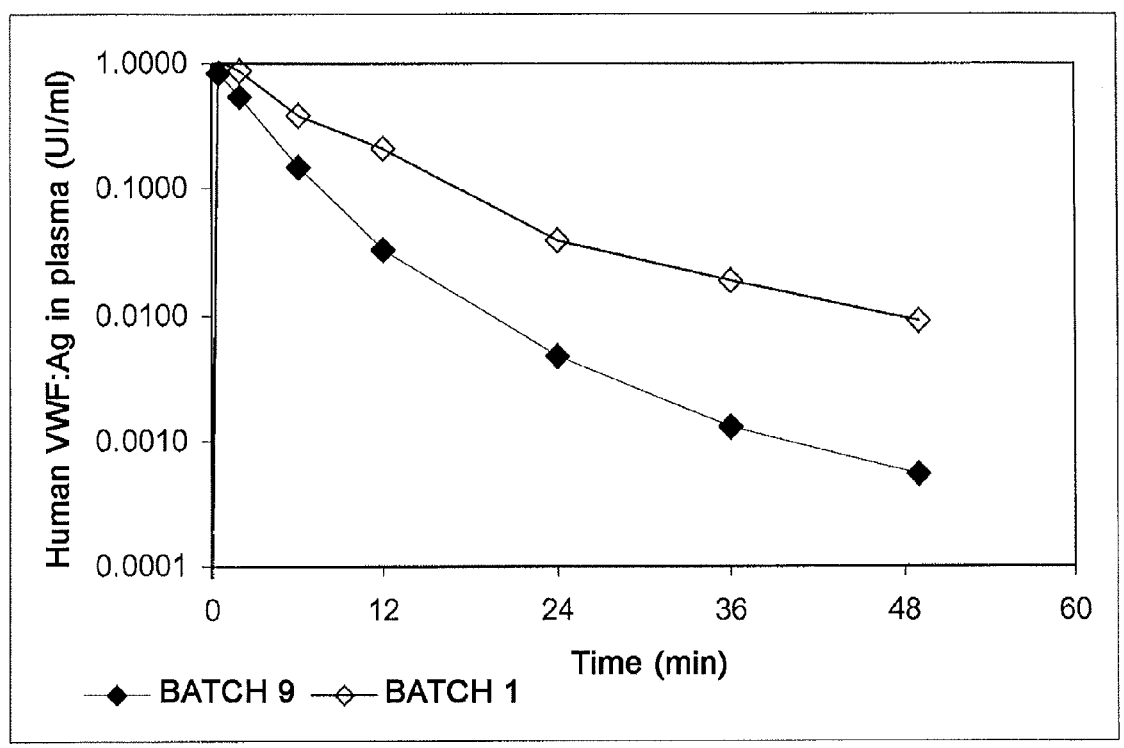
FIG. 3 shows the pharmacokinetics of human VWF:Ag in rabbit plasma after the administration of unencapsulated FVIII and after the application of the composition.

The spray drying process has been used for the production of alginate microparticles as described in Erdinc B. I. [Erdinc B. I. (2007) Micro/nanoencapsulation of proteins within alginate/chitosan matrix by spray drying, Degree Thesis, Queen's University, Kingston, Canada]. Basically, microparticles were prepared by producing an emulsion with the polymer and the active ingredient chosen.

A Büchi Mini Spray Dryer B-290 device was used for spraying the samples under the following conditions: spray temperature: 140° C.-180° C., intake rate: 35-40 m³/h, injection flow rate: 3.5-5 ml/min and pressure 4-6 psi.

EXAMPLE 2

Description of the Microparticles

Tables 1, 2 and 3 describe the materials used in the manufacture of microparticles and their features, including size, Z potential and yield. The manufacturing process and the conditions used were as described in Example 1.

TABLE 1

Description of FVIII microparticles (plasmatic FVIII)

| Batch | Polymer | Mean particle size (µm) | Z Potential (mV) |
|---|---|---|---|
| BATCH 1 FVIII | Sodium Alginate | 3.6 | −32 |
| BATCH 2 FVIII | Sodium Alginate | 4.5 | −32 |
| BATCH 3 FVIII | Sodium Alginate | 4.7 | −31 |

The FVIII activity/FVIII antigen ratio gives an idea of the proportion of active protein in a given sample. In this way, if we compare the activity/antigen ratio in the initial sample with that obtained in the encapsulated sample, we can calculate the proportion of active ingredient which remains functional after microencapsulation. In the example, we found that the activity yields during the process of encapsulation, expressed as a percentage compared to the initial activity yield, are 57.6%, 33.9% and 35.7% for batches 1, 2 and 3 respectively.

TABLE 2

Description of FIX microparticles (plasmatic FIX)

| Batch | Polymer | Mean particle size (µm) | Z Potential (mV) |
|---|---|---|---|
| BATCH 4 FIX | Sodium Alginate | 4.9 | −63 |
| BATCH 5 FIX | Sodium Alginate | 4.5 | −18 |
| BATCH 6 FIX | Sodium Alginate | 4.9 | −10 |

In this case, we found that the activity yields during the process of encapsulation in batches 4, 5 and 6, are 100% in all said batches.

TABLE 3

Description of rFVIII microparticles ($_{recombinant}$FVIII) and rFVIIa ($_{recombinant}$FVIIa)

| Batch | Polymer | Mean particle size (µm) | Z Potential (mV) |
|---|---|---|---|
| BATCH 7 rFVIII | Sodium Alginate | 4.7 | −70 |
| BATCH 8 rFVIIa | Sodium Alginate | 4.9 | −64 |

In the case of proteins of recombinant origin, the activity yields determined during the process of encapsulation were of 25% and of 71% for batches 7 and 8 respectively.

In all batches, the size of particle was determined with the Beckman Coulter LS13320 device through a diffraction laser and the Z Potential was measured with the Malvern Zetasizer device.

The biological activity of FVIII was determined by deficient plasma clotting assay or by evaluating the generation of FXa by chromogenesis. In the case of FVIIa and FIX, the biological activity was determined by evaluating the clotting time (partial activated thromboplastin time) of plasmas without FVII and FIX, respectively. The protein concentration was determined by the immunological detection method of enzyme-linked immunosorbent assay (ELISA) using specific antibodies against FVIII:Ag, FIX:Ag or FVII:Ag respectively.

The activity/antigen ratios, indicative of the proportion of active protein in a given sample were calculated by obtaining the quotient between the activity and antigen units for the specific active ingredient in the sample. The calculation of the activity/antigen yield is carried out by estimating the percentage of variation between the activity/antigen ratios of the starting sample and of the final encapsulated product.

As can be seen in all cases, the average particle size is less than or equal to 5 μm and the Z Potential is negative. Also the results of activity/Ag yield indicate that the biological activity during the process is being maintained.

The various tables show that the controlled release system is suitable for different active ingredients.

EXAMPLE 3

In Vitro Release Test

A controlled release test with a continuous flow cell is performed in a Sotax CE1 device in closed circuit in order to evaluate the release of active ingredient.

The test was conducted at a temperature of 37° C. with a flow rate of 7-25 ml/min using as a dissolving medium an imidazole pH 7.3 buffer containing 1% human albumin. A representative sample was extracted for analysis at different times (5 minutes, 10 minutes, 15 minutes, 30 minutes, 60 minutes, 120 minutes, 180 minutes and 240 minutes). The volume of extracted sample was replaced with the same volume of fresh medium in order to correct the loss of volume.

The biological activity of FVIII was determined by a deficient plasma clotting assay or by evaluating the generation of FXa by chromogenesis. In the case of FVIIa and FIX, the biological activity was determined by evaluating the clotting time (partial activated thromboplastin time) of plasma without FVII and FIX, respectively. The protein concentration was determined by the immunological detection method of enzyme-linked immunosorbent assay (ELISA) using specific antibodies against FVIII:Ag, FIX:Ag or FVII:Ag respectively.

After completion of the test the following results were obtained:

TABLE 4

In vitro release test of unencapsulated lyophilised FVIII (BATCH 9)
BATCH 9 (unencapsulated)

| Time (min) | FVIII: C released (%) |
|---|---|
| 5 | 100 |

TABLE 5

In vitro release test of FVIII nanoparticles (BATCH 1)
BATCH 1 (encapsulated)

| Time (min) | FVIII: C released (%) |
|---|---|
| 5 | 20.7 |
| 10 | 29.6 |
| 15 | 35.2 |
| 30 | 40.5 |
| 60 | 51.7 |
| 120 | 63.0 |
| 180 | 69.0 |
| 240 | 71.0 |

We can see that the composition of the microparticle applied to the active ingredient modifies the release kinetics of the product compared to unencapsulated product.

EXAMPLE 4

Pharmacokinetics of Factor VIII in Animals

In order to evaluate the effect of the composition on the release of active ingredient in vivo, a pharmacokinetics test was carried out on rabbits. For this, a dose of 50 IU/kg of human FVIII from Batch 9 (not encapsulated) was administered intravenously to three female New Zealand White rabbits. Similarly, a dose of 50 IU/kg of encapsulated FVIII from Batch 1 as manufactured as described in example 1 and described according to example 2 was administered intravenously to a further three female New Zealand White rabbits. At various times, plasma samples were obtained which were analysed to detect the presence of human FVIII:C, as described in Table 6. The detection of human FVIII was performed by chromogenesis after selective immunological capture of the human FVIII molecules. This allows the activity of infused human FVIII to be distinguished from that of rabbit FVIII.

TABLE 6

Pharmacokinetics of human FVIII: C in rabbit plasma after the administration of unencapsulated FVIII and after the application of the composition

| Time (hours) | FVIII (unencapsulated) BATCH 9 hFVIII: C (U/ml) | FVIII microparticles (encapsulated) BATCH 1 hFVIII: C (U/ml) |
|---|---|---|
| 0 | 0.018 ± 0.024 | 0.046 ± 0.012 |
| 0.5 | 0.931 ± 0.069 | 0.459 ± 0.186 |
| 2 | 0.678 ± 0.236 | 0.534 ± 0.158 |
| 6 | 0.238 ± 0.165 | 0.346 ± 0.076 |
| 12 | 0.054 ± 0.062 | 0.243 ± 0.005 |
| 24 | 0.023 ± 0.027 | 0.090 + 0.008 |
| 36 | 0.022 ± 0.024 | 0.073 ± 0.009 |
| 49 | 0.021 ± 0.026 | 0.033 ± 0.011 |

We can see from the results that the composition delays the release of the active ingredient in plasma. In addition, these results demonstrate that there is no cell mechanism (liver, spleen, or macrophages) which rapidly removes the microparticles from the circulation, in spite of their size.

The analysis of this data using appropriate software for this purpose (WinNonlin 5.2) allowed us to calculate the pharmacokinetic constants detailed in table 7.

TABLE 7

Pharmacokinetic parameter of human FVIII: C in rabbit plasma after the administration of unencapsulated FVIII and after the application of the composition

| | | FBI (unencapsulated) BATCH 9 | FVIII microparticles (encapsulated) BATCH 1 |
|---|---|---|---|
| FVIII: C | Half-life (h) | 3.0 ± 1.6 | 12.7 ± 2.7 |
| | Average residence time (h) | 5.1 ± 1.1 | 17.4 ± 3.8 |

EXAMPLE 5

Pharmacokinetics of the Von Willebrand Factor in Animals

Both in the case of the BATCH 9 preparation (unencapsulated FVIII) and in the preparation of Batch 1 (encapsulated FVIII), the FVIII was of plasma origin with a significant content of von Willebrand factor (VWF). This means that the encapsulation of the VWF occurs at the same time as the encapsulation of FVIII. For this, their behaviour can be studied independently. For this we proceeded to independently analyse the VWF pharmacokinetics, by assessing the presence of the human VWF antigen (VWF:Ag) in the rabbit plasma. The results are shown in Table 8.

TABLE 8

Pharmacokinetics of human VWF: Ag in rabbit plasma after the administration of the unencapsulated VWF and after the application of the composition

| Time (hours) | FVIII/VWF (unencapsulated) BATCH 9 VWF: Ag (Ul/ml) | FVIII/VWF microparticles (encapsulated) BATCH 1 VWF: Ag (Ul/ml) |
|---|---|---|
| 0 | 0.000 ± 0.000 | 0.000 ± 0.000 |
| 0.5 | 0.859 ± 0.193 | 1.053 ± 0.048 |
| 2 | 0.552 ± 0.247 | 0.862 ± 0.055 |
| 6 | 0.150 ± 0.080 | 0.384 ± 0.106 |
| 12 | 0.033 ± 0.022 | 0.207 ± 0.031 |
| 24 | 0.005 ± 0.002 | 0.040 ± 0.005 |
| 36 | 0.001 ± 0.000 | 0.019 ± 0.008 |
| 49 | 0.001 ± 0.000 | 0.009 ± 0.005 |

We can see from the results that the composition delays the release of the active ingredient in plasma. In addition, these results demonstrate that there is no cell mechanism (liver, spleen, or macrophages) which rapidly removes the microparticles from the circulation, in spite of their size.

The analysis of this data using appropriate software for this purpose (WinNonlin 5.2) allowed us to calculate the pharmacokinetic constants detailed in Table 9.

TABLE 9

Pharmacokinetic parameter of human VWF: Ag in rabbit plasma after the administration of unencapsulated FVIII/VWF and after the application of the composition

| | | FVIII (unencapsulated) BATCH 9 | Microparticles of FVIII (encapsulated) BATCH 1 |
|---|---|---|---|
| VWF: Ag | Half-life (h) | 5.7 ± 0.3 | 11.1 ± 2.8 |
| | Average residence time (h) | 3.6 ± 0.5 | 11.9 ± 3.7 |

As can be observed, the encapsulation of the active ingredient, VWF in this case, significantly extends its half-life.

While the invention has been described for examples of preferred embodiments, these should not be considered limitative of the invention which will be defined by the broader interpretation of the following claims.

The invention claimed is:

1. A biocompatible composition for intravenous administration comprising microparticles of alginic acid or salt thereof less than or equal to 5 μm in size and having a negative Z potential, and wherein the alginic acid or salt thereof is complexed with a therapeutic active ingredient.

2. A composition according to claim 1, wherein the size of the microparticles is between 1 and 4.5 μm.

3. A composition according to claim 1, wherein the Z potential is between −70 and 0, not including 0.

4. A composition according to claim 1, wherein the active ingredient is a peptide, a protein or a hormone.

5. A composition according to claim 4, wherein the active ingredient is of human, animal, recombinant or transgenic origin.

6. A composition according to claim 4, wherein the active ingredient exhibits labile biological activity.

7. A composition according to claim 4, wherein the active ingredient is a blood clotting factor.

8. A composition according to claim 4, wherein the active ingredient is factor VIII.

9. A composition according to claim 4, wherein the active ingredient is VWF.

10. A composition according to claim 4, wherein the active ingredient is the complex formed by FVIII and VWF.

11. A composition according to claim 4, wherein the active ingredient is factor IX.

12. A composition according to claim 4, wherein the active ingredient is factor VIIa.

* * * * *